United States Patent [19]
Mahrer

[11] Patent Number: 6,059,972
[45] Date of Patent: May 9, 2000

[54] APPARATUS FOR RECEIVING AND CONDITIONING ORGANIC WASTE BY ANAEROBIC BIOCONVERSION

[76] Inventor: François-Régis Mahrer, 61, rue de Frémis, Case Postale 28, CH-1241 Puplinge, Switzerland

[21] Appl. No.: 08/981,833

[22] PCT Filed: Jul. 18, 1995

[86] PCT No.: PCT/IB95/00568

§ 371 Date: Aug. 21, 1998

§ 102(e) Date: Aug. 21, 1998

[87] PCT Pub. No.: WO96/02469

PCT Pub. Date: Feb. 1, 1996

[51] Int. Cl.[7] .................................................. C02F 3/28
[52] U.S. Cl. .................... 210/603; 210/610; 210/613; 210/149; 210/173; 210/181; 210/256; 48/197 A
[58] Field of Search .................................. 210/601, 603, 210/605, 610, 612–614, 630, 739, 741, 743, 744, 103–105, 141, 149, 173, 181, 205, 256; 48/197 A

[56] References Cited

U.S. PATENT DOCUMENTS

| | | |
|---|---|---|
| 4,165,285 | 8/1979 | Wind et al. . |
| 4,204,842 | 5/1980 | Morel et al. . |
| 4,225,457 | 9/1980 | Schulz . |
| 4,274,839 | 6/1981 | Leas . |
| 4,289,625 | 9/1981 | Tarman et al. . |
| 4,350,588 | 9/1982 | Tsubota . |
| 4,451,372 | 5/1984 | Rovira . |
| 4,493,770 | 1/1985 | Moilliet . |
| 4,604,206 | 8/1986 | Sullivan . |
| 4,632,692 | 12/1986 | Lebesgue et al. . |
| 4,632,758 | 12/1986 | Whittle . |
| 5,256,378 | 10/1993 | Elston . |
| 5,338,452 | 8/1994 | Pidaparti . |
| 5,409,610 | 4/1995 | Clark . |
| 5,492,624 | 2/1996 | Rozich . |
| 5,514,277 | 5/1996 | Khudenko . |
| 5,525,228 | 6/1996 | Dague et al. . |
| 5,633,163 | 5/1997 | Cameron . |
| 5,645,725 | 7/1997 | Zitzelsberger et al. . |

Primary Examiner—David A. Simmons
Assistant Examiner—Fred Prince
Attorney, Agent, or Firm—Henderson & Sturm LLP

[57] ABSTRACT

A tank (1) for an apparatus for receiving and conditioning organic waste by anaerobic bioconversion, in particular, waste produced by restaurant kitchens and other facilities, includes a main enclosure wherein bioconversion takes place, and a secondary enclosure (18) for receiving and storing ground organic waste before it is transferred to the main enclosure for completion of its bioconversion. A hopper (4) or other device for receiving the organic waste is associated with a grinder (2) and is connected to the secondary enclosure (18) of the tank for feeding the ground organic waste. A recirculation system (12, 15) for recycling the contents of the tank includes a pump (13), means for distributing (17a, 17b) the contents of the main enclosure between the different levels thereof, and separate means (9, 22) for removing solid residues and liquid waste.

25 Claims, 2 Drawing Sheets

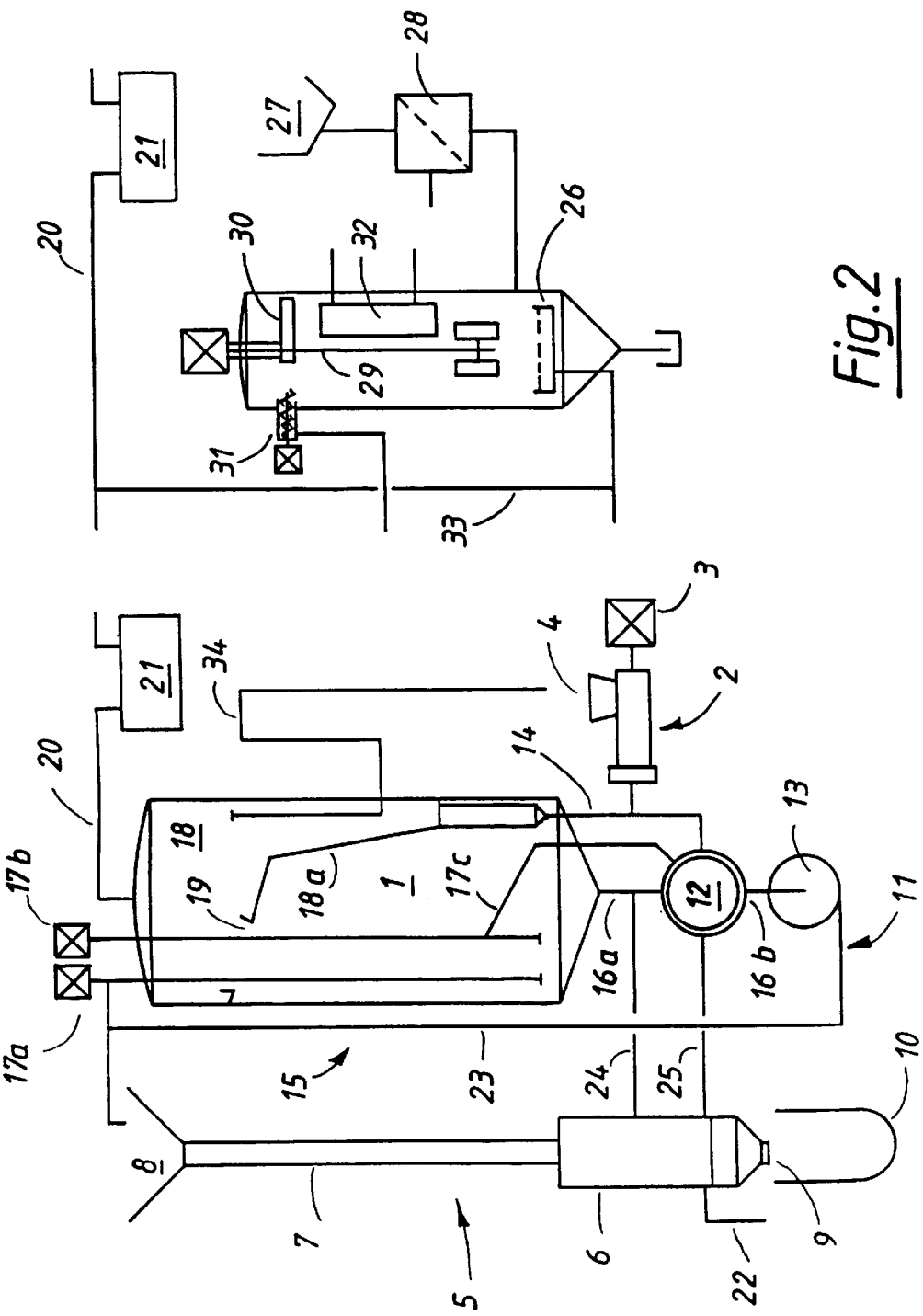

APPARATUS FOR RECEIVING AND CONDITIONING ORGANIC WASTE BY ANAEROBIC BIOCONVERSION

FIELD OF THE INVENTION

The invention relates to an apparatus for receiving and conditioning organic waste that operates by anaerobic bioconversion, as well as a process for treating a flux of organic waste in this apparatus. The principal application of the invention is the treatment of waste produced by restaurant kitchens and other facilities, but other applications are also possible.

BACKGROUND OF THE INVENTION

The reduction and elimination of, or the recovery of energy from, organic waste from urban activities is a problem that can be approached from several angles, the studies resulting therefrom leading to varying solutions according to the importance attached to the different parameters under consideration.

Formerly, food waste was sold to serve as animal feed. Today, this traditional mode of recycling food waste has given way to a policy of destruction, which is much more expensive. In parallel, there is a growing tendency to increase the intermediate stockage time for waste food, in order to allow more time between collection operations whose cost is also ever increasing.

The solutions imagined to date to combat the risks associated with food waste waiting for collection are refrigeration or partial sterilization using chemical products; both involve the temporary and costly slowing of an uncontrolled biological activity.

In contrast to procedures in use heretofore, the present invention provides for a local and immediate treatment of organic matter to carry out controlled biological processes in a specially designed digestor.

The present invention principally takes into account the mass of kitchen waste to be managed by restaurants serving a large number of meals. The invention is derived from two considerations:

On the one hand, making available to these facilities an anerobic digestor that, while being as compact as possible is able to receive the mass of waste and continually restitute therefrom waste waters, concentrated solid residues and biogas of high-quality (from the point of view of good calorific value and combustibility), responds to a real need.

On the other hand, water purification stations, composting apparatus or other installations of the same type operate conventionally based on the principle that fluxes of organic waste are collected on as large a scale as possible and delivered to a center where the bioconversion process takes place in relatively stable conditions.

Stability is indeed an essential condition for maintaining the biological process for transforming the materials.

SUMMARY OF THE INVENTION

Taking into account the flux of kitchen waste produced in restaurants or other facilities of the same type, the present invention departs from the principle set out above. It aims to install "digestors" at the very sites where the waste is produced and proposes a treatment system which, by carefully acting on the digestor's dynamics, enables the bioconversion process to be sustained, despite any temporary quantitative or qualitative variations or irregularities in the flow of waste to be treated.

In this manner, the food waste will be treated before it has enough time to develop any pathogenic activity. Thanks to the action of micro-organisms and the methanogenetic process, its potential energy will be converted to a valuable product, biogas.

The principal idea of the invention is to create an apparatus for the treatment of organic waste that can be operated precisely and at will, so that the treatment process takes place as efficiently as possible, despite variations in the flux of waste to be treated.

To this end, the first object of the invention is an apparatus according to claim 1, and its second object a process according to claim 14. Further characteristics of the invention are set out in the dependent claims.

The tank according to the invention comprises a main enclosure where bioconversion takes place, and a secondary enclosure for receiving and storing organic waste before it is transferred to the main enclosure to complete bioconversion.

As the organic waste is produced, for instance in a kitchen, it is introduced into a receiving device, ground by means of a grinder or other mechanical disintegration means, and the ground waste is fed into the tank's secondary enclosure.

The capacity of the secondary enclosure 18 can correspond at least to the maximum quantity of ground waste treated per day. It is normally filled once per day and the daily mass of waste will remain in the secondary enclosure for about a day. During its stay in the secondary enclosure, the waste is pre-heated and begins a first phase of gas production, without releasing unpleasant odors. This ground waste in the secondary enclosure forms a homogeneous mass, whose homogeneity can be maintained or improved by recirculation or mixing by means of recirculation circuits described below.

Then, metered transfers of the contents of the secondary enclosure into the main enclosure are made as a function of the progression of bioconversion, by means of a system of circuits for recirculating the contents of the main enclosure and the secondary enclosure.

The system of recirculation circuits includes a pump and means for distributing the content of the main enclosure between different levels thereof, which enables taking off and injecting amounts of the content of the main enclosure at selected levels according to parameters of the biomethanisation process.

The main enclosure of the tank where biomethanisation takes place contains a stratified nonhomogeneous fluidic mass having a spongy layer floating on its free surface, with an accumulation of dense sludge at the bottom. By taking off and injecting amounts of this stratified fluidic mass at selected levels, it is possible to control the conditions of biomethanisation continuously and reliably.

The system of recirculation circuits also includes discrete means for extracting solid residues and spent liquids, enabling intermittent removal of metered amounts of selected parts of the contents of the main enclosure via extraction means where the solids and liquids are recovered.

To maintain the contents of the main enclosure in equilibrium, each amount removed via the extraction means will be followed by the transfer of a more-or-less equivalent amount of ground waste from the secondary enclosure into the main enclosure. This enables progressive feeding of the main enclosure with metered amounts of a pre-heated homogeneous mass, hence without any thermic shock liable to affect the equilibrium of the biomethanisation process which in particular requires great thermic stability.

The secondary enclosure is preferably separated from the main enclosure by a separating partition located inside the tank, the main and secondary enclosures being capped by a common top zone for the collection of biogas. Advantageously, this partition includes an inclined upper portion enabling solid matter floating in the main enclosure to overflow into the secondary enclosure, this inclined portion of the partition being perforated to allow liquids to filter into the main enclosure. In this manner, solid matter which has not been digested during the biomethanisation process drops into the secondary enclosure where it is mixed with the ground waste stored therein, to later be recycled into the main enclosure.

As the biogas leaves the tank, by measuring its $CO_2/CH_4$ ratio for instance by spectrometric or calorimetric analysis of a burner flame, it is possible to evaluate the carbon/nitrogen ratio of the waste in the tank's main enclosure, thereby enabling actuation of an auxiliary feed device arranged to feed into the tank metered amounts of an additive material ("supplement"), in particular water, carbon-containing matter or nitrogen-containing matter. This device may for example include a device for separating fat from fatty waste water, connected directly or indirectly to the secondary enclosure.

BRIEF DESCRIPTION OF THE DRAWINGS

We will now describe, by way of example, a main embodiment of the digestor, and several possible variations, as well as a manner of carrying out the method. For this, reference is made to the drawings, wherein:

FIG. 1 is a simplified schematic representation of a digestor;

FIG. 2 is a simplified schematic representation of a separator that can be associated with the digestor of FIG. 1.

PREFERRED EMBODIMENTS

Figure 3:
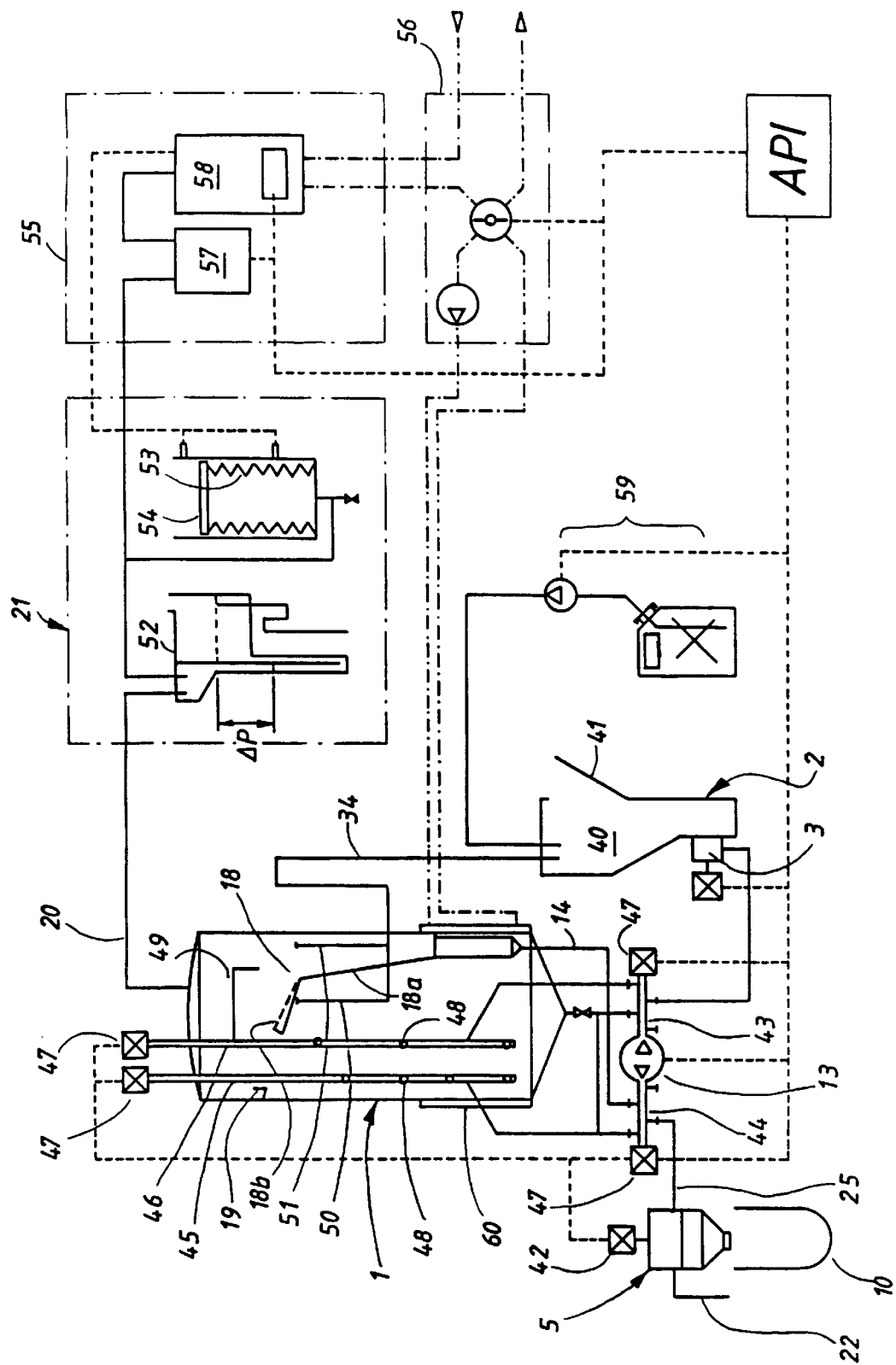
FIG. 3 is a schematic representation of a variation.

FIG. 1 shows the principal components of an embodiment of the digestor. It comprises a closed tank 1 wherein the anerobic bioconversion takes place. This tank 1 may be made of stainless steel sheet, or of plastic material. When for example the duration of the transformation cycle is about 10 days, and the amount of waste to be treated is on average 25 liters per day, the tank will have a capacity of about 500 liters at least, so the level of the mass of waste can fluctuate without obstruction. The tank is generally cylindrical, with a dome on its upper part to allow the accumulation of a gas phase, in principle a mixture of methane ($CH_4$) and carbon dioxide ($CO_2$), and a conical bottom at its base to facilitate the evacuation and circulation of sludge.

A feed unit 2 is arranged to feed waste to be treated into the tank 1. Unit 2 is in the form of a grinder driven by a motor 3 and equipped with a feed hopper 4. The grinder drives the waste loaded into the hopper 4 into the tank 1. As needed, the feed unit could have different constitutions. Several variations will be described later.

A separator unit 5 forms an additional enclosure connected to the tank 1, arranged such that the principle of communicating vessels provides balancing of levels between the tank and the separator, whereby the difference of the levels between these two parts of the digestor corresponds to the gas pressure in the tank. At its lower part, the separator unit 5 includes a cyclone or centrifuge 6 which controls concentration of the solid phase that will be extracted at this location. In certain cases, this separation unit can be a simple decanter.

Above the separator unit 5 extends a column 7 wherein the stabilised liquid phase accumulates. At the top of this column is an overflow funnel 8. The solid phase of residues separated in the unit 5 is extracted via a valve 9 and drops into a container 10 equipped with draining means, for example exchangeable permeable bags that can be fitted to allow draining of the residues and their removal. In the case where the member 6 is a centrifuge, the separator unit will be equipped with an outlet 22 for the liquid phase and a flap (not shown) through which the solid phase can be removed in the form of cylindrical briquettes.

An important part of the described installation is the recirculation unit 11. This includes a multi-way distributor 12, a recirculation pump 13 and various pipes interconnecting the digestor's components. First, a T-shaped pipe 14 interconnects the outlet of grinder 2, on the one hand to the inlet of a secondary enclosure 18 inside the tank 1, and on the other hand to an inlet of distributor 12. It is hence possible to feed ground waste into the secondary enclosure 18, where the waste can remain waiting in the presence of gas already formed by preheating and homogenization, to then be transferred as metered amounts of homogeneized and preheated mass of waste into the principal enclosure via the distributor 12, pump 13 and recirculation circuit 15.

The recirculation circuit 15 constitutes means by which the biomethanisation process can be precisely controlled. It is a system of piping provided with the necessary valves and notably with control members 17a and 17b. In the example of FIG. 1, it consists of the following:

Two piping segments 16a and 16b connect respectively the bottom of the tank 1 to the multi-way valve 12, and the latter to the intake of pump 13. The section 23 of circuit 15 connects the outlet of pump 13 on the one hand to the inlet of member 17a, and on the other hand to an overflow tap in the overflow funnel 8. Lastly, connector sections 24 and 25 connect the separator unit's cyclone or centrifuge 6 on the one hand to piping 16a and on the other hand to distributor 12.

The members 17a and 17b, which are parallel to one another, plunge into the tank 1. They each have the form of a rod-like assembly formed of concentric tubes one of which can be rotated by means of a motor situated at the top of the member. These tubes are provided with coinciding openings at different levels so that, depending on the relative orientation of the tubes, the fluid in the inner tube can pass out into the tank at a given level, or fluid in the tank can pass into the tube, also at the desired level. The rod-like assembly 17b is connected to the multi-way distributor 12 by a connexion 17c. Hence, thanks to the distributor assembly 12, 17a, 17b, the circuit 15 enables fluid in the tank to be taken off at a desired level, to be delivered to the output unit 5, or to be recirculated at any given level in the tank.

The inner partition 18a separating the auxiliary enclosure 18 from the remainder of the tank includes an upper part formed of an inclined flat plate provided with an opening 19. A lower part in the form of a tube of relatively large diameter extends down below the secondary enclosure 18 where the grinder 2's outlet, leading into the pipe 14, penetrates into the tank.

Thus, the digestor's main enclosure and secondary enclosure 18 can be fed, mixed, interconnected and emptied by the described recirculation system.

Lastly, the tank's dome is connected by an extractor piping 20 to a processing unit 21 supplying biogas ready for later use. Depending on the size of the envisaged application, i.e. the quantity of waste to be treated, biogas, which is nothing but a renewable form of natural gas, will be delivered to a water heater, or to a heat-exchange unit.

The unit 21 comprises a water separator, a safety valve and a flow meter. A hydraulic valve having a water column of given adjustable height, through which the gas passes by lubrication, is also integrated into the unit 21. This valve regulates the pressure in the tank 1. If needed, a means for testing the combustibility of the gas can also be provided.

Division of the digestor into a feed unit 2, a recirculation unit 11, a separation and extraction unit 5, and a gas processing unit 21 allows a flexible and efficient control of the digestor as a function of three criteria:

Physical criteria: formation of well separated solid, liquid and gas phases;

Chemical criteria: production of combustible gas providing an appreciable saving of energy; and Biological criteria: sustainment of efficient life conditions for bacterial species.

From the structural point of view, a particularly compact arrangement is obtained by positioning the entire recirculation unit 11 below the tank 1, in the form of a tank-supporting base member. The entire unit can be arranged inside a cabinet-like container, wherein the input hopper 4 is for example accessible behind a flap-door like those fitted on certain garbage containers.

As a variation, the tank 1 and the extractor means are enclosed in a closed ventilated volume, such as a cabinet, and the waste-receiving device, for instance a container with a flap-door as well as the grinder 2, are arranged outside this cabinet at a location closer to where the waste is produced, and are connected to the tank 1 by a flexible tubing. For example, such an arrangement would enable the waste-receiving device to be located in a kitchen, whereas the cabinet/tank is situated in an adjacent place.

To avoid bad smells escaping or risks in case of gas leakage, the upper part of the housing forms a compartment fitted with means for ventilating the entire apparatus.

Auxiliary devices to be provided include instruments for measuring important parameters: pressure, temperature, level, pump and grinder flowrates and, possibly, the pH. They also include control means enabling actuation at will of the elements of the distributor assembly, pump 13, separator 6, etc, as well as of heating bodies for maintaining the tank at the desirable temperature (35 to 55° C.).

The digestor as described above can operate efficiently in numerous different conditions. The feed unit 2 can include, in addition to the grinder, a pump outputting a mixture of preconditioned waste into the pipe 14. The pressure in the tank 1 is adjusted by the unit 21 as indicated above, and a siphon means 34 automatically removes the surplus of fluid waste accumulating in the enclosure 18. This surplus drops into the input hopper 4 of the shredder or grinder, providing a signal to personnel who feed waste into the apparatus that the apparatus is momentarily saturated.

As a variation, it is also possible to provide an arrangement wherein the supply unit is replaced by a two-level device whose hopper supplies a centrifugal shredder able to deliver the mass of waste into a secondary compartment arranged at the top, exposed to the air. This compartment can be fitted with an overflow and constitutes, with the input hopper, a closed circuit enabling the ground waste to be circulated/mixed while it is waiting to be delivered by the grinder 2 to the tank's enclosure 18. With such an arrangement, it has been observed that during a waiting period a first aerobic heat-producing bioconversion takes place in the mass of waste exposed to the air.

The described construction can be designed in modular form. If required, several tanks 1 of the same dimensions can be connected in parallel to increase the capacity. A modular construction enables digestors to be arranged in an optimal manner, adapted from case to case to the particular treatment conditions.

As for all foodstuffs, kitchen waste consists principally of quatenary products containing the elements carbon, hydrogen, oxygen and nitrogen, or ternary products containing carbon, hydrogen and oxygen. However, for a proper maintenance of bacterial species in a digestor, the C/N ratio should be controlled to maintain it at a suitable value.

Kitchen waste from a restaurant represents a flux of matter which is basically variable in quantity and composition.

The operation of the described system thus implies knowlege of the variations to be expected in each particular case, which enables a control program for the digestor to be established.

The restaurant personnel will be instructed to tip the waste into the hopper 4 progressively as the waste is produced. The grinder 2 can be automatically controlled, for example in response to the detection of the presence of a mass in the hopper 4. Its control can also be manual or by timer.

As indicated above, the ground flux leaving the grinder 2 is stored for preheating and homogenization during a waiting period in the secondary enclosure 18. In certain cases, control of the process can be entirely automated. At each moment, the instantaneous state of the process is represented by a set of data supplied by measuring means. A comparison of this data with predetermined threshold values enables a determination of when and how the extraction means and/or the recirculation means should be actuated, possibly also the heating means and the auxiliary feeding means.

The introduction of ground kitchen waste into the main enclosure of a tank as described creates a fluid mass that has a tendency to stratify. At the free surface, a layer of spongy or emulsified structure is formed, whereas dense sludge accumulates at the bottom of the tank. The biochemical process takes place in a median zone, with release of gas bubbles which collect in the upper common zone belonging to the main and secondary enclosures, in which zone the gas-releasing potential creates a given pressure inside the tank.

The stabilized liquid phase will be extracted via the piping 22 and removed via waste water drainage system. The solid phase usually has only a very small volume. It can be compacted and removed using a bag placed in the container 10.

As regards the stabilized gas phase, to a certain extent its composition depends on how the bioconversion is controlled. This combustible gas can be collected and stored for subsequent use. However, it can also be immediately used in situ by feeding it to a water heater burner, for example a condensation-type water heater including recovery of the latent heat of the combustion gases. The hot water produced can be used to maintain the tank hot, or for any other purpose. This use has the advantage of considerably simplifying the gathering of data relative to the composition and characteristics of the biogas produced in the digestor, because analysis of the burner flame, for instance by optical means, immediately provides the required data.

The control of the process includes metered transfers of temporarily stored matter from the enclosure 18 into the main enclosure, possibly with the addition of supplements, and the recirculation of given portions of the fluid mass in the main enclosure, by taking off a mass at a given level and reinjecting it at another level. Thanks to the means 17a, 17b, this recirculation takes place without undue disturbance of the zone wherein the biological activity is taking place.

The level of the fluid mass in the main enclosure can rise up to the opening 19 and overflow into the secondary enclosure. Preferably, the oblique portion of partition 18a has a grid structure, which enables filtration: the liquid phase returns back into the main enclosure, whereas the non-digested solids from the main enclosure drop into the secondary enclosure 18 and are mixed with the temporarily-stored ground waste.

All of the monitoring operations can if required be remote controlled from a control station by means of telemeasurement and telecontrol devices. In certain cases, where the conditions for supplying waste are sufficiently well established, control programs can be set up.

In cases where it is desired to treat waste from relatively large restaurant kitchens, for instance say those serving on average more than 300 meals per day, the above-described compact construction can unexpectedly result in a significant simplification in the usual water-treatment installations and operations.

It is known that the elimination of fatty waste water is a burdensome task in restaurants of a given size. To avoid fouling of the piping, the installations must include a device for separating fats from liquids that can be removed with waste waters. These separators generally include two chambers, one to retain/decant heavy particles, and one for flottation of fatty matter. Periodically, they have to be emptied and cleaned out, these operations unfortunately generating foul smells.

However, the digestor as described above can easily be associated with a fatty matter separator as shown in FIG. 2. In this way, the treatment of fatty waste water is dissociated with operation of the digestor, and is carried out much more conveniently.

A separate tank 26 is provided for the flottation of fatty matter. Residual water from dish washing, by hand or by machine, is delivered into a receiving basin 27 from where it flows out into a grid separator 28 where solid matter is removed and delivered to hopper 4. The fatty waste waters then go into an assisted flottation tank 26 wherein a stirrer 29 turns them at controlled rate. An evacuator means 30, rotated by the same motor as the stirrer 29, turns at the level of the liquid in the tank, where floating fatty matter accumulates. An extractor 31 delivers it to the hopper 4 (and from there to the digestor's enclosure 18), whereas the waste water is removed either from the bottom of the flottation tank, or via piping (not shown) connected to the body of the flottation tank.

Two auxiliary devices considerably improve the efficiency of the described separator. These are a heat exchanger 32, which cools the separator and thus recovers heat from the washing machine water, while facilitating solidification of the fatty matter, and a bubbling circuit 33. The latter extends from a by-pass provided in the gas pipes at the outlet of tank 1, and penetrates by a diffuser in the lower part of the flottation tank 26. A pump or compressor can be provided in this circuit to expel gas passing though the liquid mass of the fatty waste water in the separator, which gas returns to the outlet piping 20. This operation washes the gases, increases the proportion of methane (because $CO_2$ is more soluble in water than $CH_4$), and contributes to a better separation of the fatty matters.

The residual water also benefits from the operation because its carbon content is increased which enables it to be used, if wanted, as a carbon vector to promote vegetable growth. A bubbling circuit analogous to the just-described one can also be connected to the anaerobic biomethanisation tank, where it serves as a means for stirring and for activation of degassing by coalescence.

The recovery of fatty matter as described above enables monitoring of the C/N ratio, because fatty matter essentially contains carbon and hydrogen. Metered addition of fatty material can hence re-establish the C/N ratio and consequently enable the digestor to be operated with an increased efficiency.

Furthermore, another means can be implemented to monitor the C/N ratio in the described digestor, namely the supply of waste paper serviettes and napkins into the input hopper. These materials contain little nitrogen, much carbon and fibres. Fibres help with the extraction and separation of solid phases by a flocculant effect.

FIG. 3 illustrates a variation of the embodiment shown in FIG. 1. Similar or identical elements to those of the already-described digestor are shown, and will be designated by the same references.

Moreover, the digestor of FIG. 3 includes several additions and improvements that will emerge from the following description.

The tank 1 has substantially the same construction as that of FIG. 1, with its secondary enclosure 18, separated from the main enclosure by partition 18a with opening 19. The downwardly-extending lower part of enclosure 18 is connected to the pipe 14. The upper part of partition 18a includes a grid 18b whose purpose will be explained later.

The supply unit 2 comprises a collection receptacle 40 with a flap door 41. Into the receptacle 40 lead the outlet of a siphon means 34 and the outlet of an auxiliary feed device 59, illustrated here as a canister provided with an inlet member, circulation device or electromagnetic tap. The motor-driven grinder 3 is housed in the base of container 40.

The main differences between the embodiment of FIG. 3 and the previously described embodiment reside in the structure of the distribution and recirculation system. Here, the direction/speed of rotation of pump 13 can be reversed, so the fluid can flow in either direction and at different speeds. Also, the distributor member designated by reference 12, which was associated with two liquid offtake and reinjection devices 17a and 17b, is here composed of four members designated respectively by 43, 44, 45 and 46. These four members are of similar construction: each have a fixed tube with openings 48 distributed along its length, a rotatable tube inside the fixed tube, also provided with corresponding openings, and an indexing device that can be controlled to selectively bring each of the openings in the inside tube into coincidence with a fixed opening.

The two distributor members 43 and 44 are connected by their fixed tube to each of the pump 13's inlets. They replace member 12 of the first embodiment. Members 45 and 46 (like the members 17a and 17b) are arranged vertically in the tank's main enclosure. Four devices 47 for indexing members 43 to 46 are connected to an automatic programmable control unit API, to which are also connected data sensors monitoring the operating conditions in the apparatus, as well as drive motors for the pump 13, grinder 3 and centrifuge 5.

The upper fixed opening of member 46 is connected to a pipe 49 opening above the secondary enclosure 18.

The fixed openings of members 43 and 44 are connected to various components of the distribution system. The openings of member 43 are connected respectively to the grinder 3 for feeding waste into the temporary storage enclosure 18, to the bottom of the tank for the delivery of sludge to centrifuge 5, and to a fixed opening of member 46 for the purpose of recirculation, to be explained later, a fourth opening being provided to connect tank 1 to a second servo-controlled standby tank.

For member 44, the fixed openings are connected to the bottom of the secondary enclosure via the waste-feed pipe 14, to the centrifuge 5 via piping 25 and to a fixed opening of member 45 for recirculation; a fourth opening is also provided for connection to a standby tank.

The control, monitoring and safety elements of the apparatus will now be described.

The siphon means 34 here includes two vertical inlet tubes 50, 51, the former in the main enclosure, the latter in the secondary enclosure. These tubes extend to the same height, which determines the tank's maximum level of filling.

The two basic components of the processing unit 21 are a water separator 52, also operating as a safety valve, and an expandable bellows 53 forming both a buffer reservoir and a means for regulating pressure in the tank and in the gas circuit.

The operation of valve 52 can be seen from the drawing: Drops of water driven along the pipe 20 drip into the deepest section of the valve, which leads into an enlarged section wherein the level is controlled by an overflow tube. The difference between the two levels corresponds to the pressure set by the regulator bellows 53. The latter carries a load 54 whose weight determines the pressure in the tank 1, pipes 20, etc.

The immediate use of the biogas produced in tank 1 is controlled by units 55 and 56. Elements 57 and 58 are respectively a volumetric gas-flow meter and a water heater wherein thermal energy released by combustion of the gas is transferred to a circuit supplying a heating body 60 of tank 1, and is connected to a general circuit provided for any other use of the hot water produced. In unit 56 can be seen a circulator and a four-way valve controlled by the automatic programmable control unit API, for selecting the functions of the water heater.

Two sensors provide for keeping record of the maximum and minimum expansion states of the bellows reservoir 53 and for switching off the water heater 58 when necessary.

The counter 57 and water heater 58 are also connected to the automatic programmable control unit API to ensure qualitative control of the biomethanisation. For this, two different means are available, and elements required for at least one of these two control means are provided. One of these means consists of permanently recording the volumetric flow of gas and the thermic balance of the water heater. This enables calculation of the thermic value of the burnt gas from which its composition is known, at least approximately. It is known that biogas produced in an installation such as the described digestor is essentially a mixture of non-combustible carbon dioxide, and methane whose calorific value is known. The composition of the gas produced in the digestor at a given moment provides an indication regarding the conditions of the biomethanisation reaction. This indication, interpreted as a function of the momentaneous state of the mechanical members of the apparatus, enables the process to be controlled.

The other means for analysing the produced gas is optical observation of the burner flame. The composition of the gas can also be deduced from the flame's color, or more precisely, the magnitude of the spectral intensity of its radiation.

The method, which is also an aspect of the invention, is made up of the combination of essential operations that must be carried out for the digestor to operate as efficiently as possible, given the rhythm of feeding of the organic waste and the nature of the organic waste poured into the container 40. The conditions of biomethanisation should be maintained as stable as possible in the active zone of the tank 1; gas should be allowed to accumulate as regularly as possible in the piping 20 and the buffer reservoir 53; and liquid rejects and solid residues should be regularly extracted from the tank. The operations to be carried out are divided into routine operations that are normally repeated at regular intervals; occasional operations repeated at a rhythm depending on various factors, and that should be controlled in case certain conditions prevail; and safeguard operations to be carried out to safeguard the life and the activity of the bacterial species active within the digestor, this being a priority.

The first category of operations includes:

a) Introduction of matter into the secondary enclosure 18. As mentioned previously, the grinder 3 and pump 13 act to pump the organic matter from container 40 via pipe 14 into enclosure 18. This operation can be controlled: by the personnel who empty the waste into the container; automatically; as a function of time; or as a function of the degree of filling of the container. Typically, the filling operation will be carried out at least once a day and the minimum capacity of the secondary enclosure 18 will correspond to the maximum daily amount of waste previewed for the installation.

b) The extraction of stabilized liquid removed from the main enclosure of the tank, at a height situated below the floating top-layer. This operation will be programmed so it is carried out as regularly as possible, for example at a rhythm of 5% of the average daily amount fed into the tank, every hour. The liquid is taken off via one of the openings of member 46, and expelled by pump 13 via piping 25 and overflow 22.

c) Immediately after each operation b), the same quantity of matter will be extracted from the secondary enclosure 18 via pipe 14 and injected at a selected level in the tank 1 by member 46, in order to reestablish the level to which tank 1 is filled.

The indicated rhythm for operations b) and c) will be modulated according to the data gathered. A total daily value greater or less than the fed quantity will tend to shorten or lengthen the residence time of the matter in the tank. This parameter will be factored into programming of the operation.

d) Lastly, another routine operation which is periodically controlled (especially in the case where feed from the container 40 to the enclosure 18 takes place relatively frequently) consists of turning over the structure of the piled matter temporarily stored in the enclosure 18. The most recently added portion of the content of this enclosure will be intake via the pipe 14, pump 13 and member 46 so it passes through the overflow pipe 49 and is relocated to the upper part of enclosure 18. During this operation, the liquid phase of the transported matter will be filtered by grid 18*b* and pass directly into the main enclosure of tank 1.

The second category of operations (occasional operations) includes:

a) Mixing of the matter in tank 1.

By suitably indexing the two offtake and injection members 45 and 46, liquid can be intake from a desired level in the main enclosure of tank 1 and, via distributor 44, pump 13 and distributor 43, be restitute at another level without agitating the entire liquid mass, hence without disturbing the active zone where the active bacterial population undergoes bioconversion.

b) Spraying the floating top layer.

The same elements as above also enable liquid taken from a stabilized zone to be poured onto the floating top layer to assist the integration thereof into the process.

c) The removal of solids.

As a general rule, the production of compact solid matter represents only a minor percentage of the treatment products. Sludge will be removed from the tank's base, delivered to the centrifuge 5 and, after compacting, removed via the collector vessel 10.

d) Feeding a supplement.

Should the waste with which the digestor is being fed have a composition which is systematically deficient from the point of view of a desirable chemical balance, the feeding of a supplement from the device 59 can be envisaged according to a set program. As already mentioned, the mixtures of materials fed to the digestor should maintain an equilibrium between nitrogen-based and carbon-based components, to produce biogas with a given $CO_2/CH_4$ ratio determining its energy potential. If the waste to be treated is predominantly nitrogen-based, the container 59 could consequently contain a carbon-based product, for instance an oil, and the control members will periodically inject a metered amount of this product into the container 40.

The safeguard operations consist essentially in ensuring favorable parameters for development of the active populations, namely:

a) Firstly, the digester must in all circumstances maintain an even temperature, which is achieved by the above-described operations. The temperature can from case to case be of the order of 35° C./55° C., but its variations should not exceed plus/minus 2° C. Means can be provided for signalling inacceptable variations.

b) Secondly, it is necessary to maintain a constant gas pressure in the tank, as well as in the bellows-reservoir 53 and the water heater burner, whatever may be the instantaneous composition of the biogas. This pressure is held constant by the load 54 of the bellows-reservoir 53, and any excessive extension or contraction of this member is monitored by sensors. Surplus gas can be removed by the cabinet's ventilation system, whereas a reduction of pressure can be compensated by feeding an appropriate supplement.

c) Moreover, the syphon means 34 controls any overload of the tank 1, whereas the grid 18*b* filters floating solid matter that may overflow into the secondary enclosure 18. A momentary overload is signalled by an overflow via the siphon means 34; if this happens, feed of new organic matter to the container 40 will be interrupted or reduced in order to re-establish normal functioning.

The above-described digestor has displayed a remarkable performance. With a feed of organic matter from a restaurant, the following figures have been observed:

Mean quantity treated:—50 kg/day

Weight distribution of rejects:—gas 20%—liquids 65%—solids 15%

The liquid rejects contain at least 5 g/l of organic matter and can be removed directly via the waste water disposal system. The volume of gas produced at ambient temperature and pressure is 88 l/kg of waste. The thermic output from the produced gas is 15500 Kcal/day.

What is claimed is:

1. An apparatus for receiving and conditioning organic waste that operates by anaerobic bioconversion including a biomethanization process, comprising a closed tank wherein bioconversion takes place, provided at its upper part with means for removing biogas produced, and provided with means for the discrete extraction of solid residues and liquid residues, the tank including a main enclosure wherein the bioconversion takes place, and a secondary enclosure for receiving and storing ground organic waste before the transfer thereof to the main enclosure as feed for bioconversion; the secondary enclosure being separated from the main enclosure by a partition located inside the tank; the apparatus further including a device for receiving organic waste, associated with a grinder or other mechanical disintegrating means, and connected to the secondary enclosure of the tank to feed ground organic waste into the secondary enclosure; wherein:

the separating partition is arranged to allow the storage in the secondary enclosure of a quantity of ground waste up to a variable level, and also to allow matter from the top of the main enclosure to overflow into the secondary enclosure;

the apparatus further comprises a system of circuits for recirculating the content of the main enclosure and the secondary enclosure, comprising a pump enabling inter alia metered transfer of the content of the secondary enclosure into the main enclosure, and also distribution of the content of the main enclosure between different levels therein, by distribution means; and wherein:

the apparatus is arranged so the content of the secondary enclosure is pre-heated to permit said metered transfer of the content into the main enclosure without a thermic shock liable to disturb the equilibrium of the biomethanisation process.

2. An apparatus for receiving and conditioning organic waste that operates by anaerobic bioconversion including a biomethanization process, said apparatus comprising a closed tank, said closed tank comprising an upper part comprising means for removing biogas, and means for discrete extraction of solid residues and liquid residues; a main enclosure wherein bioconversion takes place, and a secondary enclosure for receiving and storing ground organic waste for transfer to the main enclosure as feed for bioconversion wherein the secondary enclosure is separated from the main enclosure by a separating partition located inside the tank; a device for receiving organic waste associated with means for mechanically disintegrating organic waste connected to the secondary enclosure of the tank and means for feeding ground organic waste into the secondary enclosure, wherein the separating partition allows storage in the secondary enclosure of a quantity of ground waste up to a variable level, and also allows matter from the main enclosure to overflow into the secondary enclosure; a system of recirculation circuits for recirculating the contents of the main enclosure and the contents of the secondary enclosure, said system comprising a pump enabling inter alia metered transfer of the contents of the secondary enclosure into the main enclosure, and means for distribution of the contents of the main enclosure between different levels, wherein the contents of the secondary enclosure is pre-heated to permit said metered transfer of said contents from the secondary enclosure into the main enclosure without a thermic shock liable to disturb equilibrium of the biomethanisation process.

3. The apparatus according to claim 2, wherein the device for receiving waste comprises a member selected from the group consisting of an input hopper and a container with a flap door.

4. The apparatus according to claim 2, wherein the main enclosure and the secondary enclosure and the separating partition are topped by a common top zone inside the tank for the collection of biogas.

5. The apparatus according to claim 4, wherein said separating partition comprises an included upper portion enabling solid matter floating in the main enclosure to overflow as overflowing matter into the secondary enclosure, and an inclined portion perforated for filtration of liquids from said overflowing matter.

6. The apparatus according to claim 5, wherein the means for removing biogas comprises a processing unit fitted with means for monitoring parameters of biogas.

7. The apparatus according to claim 6, wherein the means for removing biogas are connected to a burner associated with a water heater, and wherein the processing unit comprises means for analyzing a burner flame.

8. The apparatus according to claim 2, wherein said means for distribution comprises circuits selected from the group consisting of at least one of an offtake circuit and a reinjection circuit provided with a plurality of inlets and outlets situated at different levels of the main enclosure, said circuits being interconnected by the system of recirculation circuits and the pump; and wherein each said offtake circuit and said reinjection circuit comprises an obturator means for selectively opening and closing each of the inlets and outlets of said circuits.

9. The apparatus according to claim 2, wherein said means for distribution comprises an overflow pipe arranged above the upper part of the secondary enclosure for circulating a most recently added part of the content of the secondary enclosure in order to turn over the structure of the piled matter temporarily stored in the secondary enclosure.

10. The apparatus according to claim 2, comprising a set of means for measuring and means for monitoring and means for controlling bioconversion, said means for controlling comprising at least one data sensor for at least one parameter selected from the group consisting of pressure in the tank, level of the mass contained in the tank, and pH.

11. The apparatus according to claim 2, comprising an auxiliary feed device for feeding a supplement to the tank, said supplement being selected from the group consisting of water, a carbon-based product, and a nitrogen-based product.

12. The apparatus according to claim 11, wherein the auxiliary feed device is arranged to meter the feed of the supplement in response to a specific means for controlling.

13. The apparatus according to claim 12, wherein the auxiliary feed device comprises a device for separating fatty matter from fatty waste water connected to the secondary enclosure.

14. The apparatus according to claim 2, wherein the tank and the means for discrete extraction are enclosed in a closed ventilated volume.

15. The apparatus according to claim 14, wherein the receiving device and the grinder are arranged inside the closed volume which is fitted with a door for feeding the waste.

16. The apparatus according to claim 14, wherein the receiving device and the grinder are arranged outside the closed volume at a location which is closer to where the waste is produced, and are connected to the tank by a flexible tubing.

17. A method for treating a flux of organic waste in an apparatus according to claim 1, situated in the proximity of a location where waste of a given category is produced, said method comprising:
    feeding waste into the receiving device progressively as the waste is produced;
    grinding the waste to form ground waste;
    feeding the ground waste into the secondary enclosure of the tank and, after a rest period; and
    feeding metered amounts of the ground waste from the secondary enclosure into the main enclosure as a function of progression of bioconversion.

18. The method of claim 17, wherein said waste comprises kitchen waste.

19. The method of claim 17, comprising taking off metered amounts of a selected part of the content of the main enclosure, and feeding said metered amounts towards means for extracting solid and liquid rejects, said taking off said amounts being followed by a transfer of a substantially equivalent quantity from the secondary enclosure into the main enclosure.

20. The method of claim 17, comprising overflowing matter from the top of the main enclosure into the secondary enclosure.

21. The method of claim 19, comprising recirculating a most recently added part of the content of the secondary enclosure as a recirculation content by said recirculation circuits and pouring said recirculated content onto the top of the secondary enclosure in order to turn over structure of piled matter temporarily stored in the secondary enclosure.

22. The method of claim 17, comprising monitoring a carbon/nitrogen ratio of the waste in the main enclosure of the tank by measuring a $CO_2/CH_4$ ratio of biogas outlet from the means for extraction associated with the tank.

23. The method of claim 22, comprising feeding metered quantities of a member selected from the group consisting of a strongly carbon-containing supplement and a nitrogen-containing supplement into the tank as a function of data supplied by monitoring the carbon/nitrogen ratio, in a manner to maintain the carbon/nitrogen ratio at an optimum value.

24. The method of claim 17, comprising combusting biogas at an outlet for heating a flow of water by released heat, evacuating combustion gas by ventilating a closed volume, and analyzing combustion in a manner to provide data representing a $CO_2/CH_4$ ratio of the biogas serving as criteria for controlling the bioconversion.

25. A method of using an apparatus according to claim 1 to treat kitchen waste.

* * * * *